(12) United States Patent
Radu et al.

(10) Patent No.: US 8,089,064 B2
(45) Date of Patent: Jan. 3, 2012

(54) AROMATIC CHALCOGEN COMPOUNDS AND THEIR USE

(75) Inventors: Nora Sabina Radu, Landenberg, PA (US); Steven W. Shuey, Chadds Ford, PA (US); Ying Wang, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 365 days.

(21) Appl. No.: 12/355,009

(22) Filed: Jan. 16, 2009

(65) Prior Publication Data

US 2009/0121627 A1      May 14, 2009

Related U.S. Application Data

(62) Division of application No. 11/014,384, filed on Dec. 16, 2004, now Pat. No. 7,504,769.

(51) Int. Cl.
*H01L 51/54* (2006.01)
(52) U.S. Cl. .................. 257/40; 257/E51.02; 313/504
(58) Field of Classification Search ............ 257/E51.02, 257/40; 313/504
See application file for complete search history.

(56) References Cited

U.S. PATENT DOCUMENTS

| 6,670,645 | B2 | 12/2003 | Grushin et al. ............ 257/98 |
| 2004/0102277 | A1 | 5/2004 | Usoro |
| 2004/0127637 | A1 | 7/2004 | Hsu et al. |
| 2005/0184287 | A1 | 8/2005 | Herron et al. |
| 2005/0205860 | A1 | 9/2005 | Hsu et al. |

FOREIGN PATENT DOCUMENTS

| WO | WO 00/70655 | 11/2000 |
| WO | WO 01/41512 A1 | 6/2001 |
| WO | WO 03/008424 A1 | 1/2003 |
| WO | WO 03/040257 A1 | 5/2003 |
| WO | WO 03/063555 A1 | 7/2003 |
| WO | WO 03/091688 A1 | 11/2003 |
| WO | WO 2004/016710 A1 | 2/2004 |
| WO | 2005052027 A1 | 6/2005 |

OTHER PUBLICATIONS

G. Gustafsson et al., Flexible light-emitting diodes made from soluble conducting polymers, Nature, vol. 357, pp. 477-479, Jun. 11, 1992.
Y. Wang, Photoconductive Polymers, Kirk-Othermer Encyclopedia of Chemical Technology, 4$^{th}$ Edition, 18:837-860, 1996.
Peter Peumans et al., Small molecular weight organic thin-film photodetectors and solar cells, Journal of Applied Physics, vol. 93, No. 7, pp. 3693-3723, Apr. 1, 2003.
Yamamoto et al., Electrically Conducting and Thermally Stable pi-Conjugated Poly(arylene)s Prepared by Organometallic Processes, Progress in Polymer Science, vol. 17, 1992, pp. 1153-1205.

*Primary Examiner* — Bernard Dentz

(57) ABSTRACT

This invention relates to dibenzothiopyran compounds. This invention also relates to layers and devices including at least one of these compounds.

6 Claims, 1 Drawing Sheet

AROMATIC CHALCOGEN COMPOUNDS AND THEIR USE

RELATED APPLICATION

This application is a division of U.S. application Ser. No. 11/014,384 filed on Dec. 16, 2004, currently pending.

FIELD OF THE INVENTION

This invention relates to dibenzothiophene, dibenzofuran, dibenzopyran, and dibenzothiapyran compounds. This invention also relates to layers and devices including at least one of the above compounds.

BACKGROUND INFORMATION

Conventional inorganic electronic devices such as cathode ray tubes are bulky and inefficient compared to alternative organic electronic devices. Organic electronic devices that emit light, such as organic light-emitting diodes (OLEDs) are potentially useful for flat panel displays. In all such organic electronic devices, an organic active layer having an organic electroluminescent compound is sandwiched between two electrical contact layers. At least one of the electrical contact layers is light-transmitting (transparent) at some wavelengths so that light can pass through the electrical contact layer and escape the device. The organic active layer emits light through the light-transmitting electrical contact layer when a voltage is applied across the electrical contact layers.

One type of organic electroluminescent device is an organic light-emitting diode ("OLED"). Some organic electroluminescent compounds that make up the active component in OLEDs include small molecules, such as organometallic complexes and dyes, and large molecules such as conjugated polymers.

OLED devices frequently include one or more charge transport and/or anti-quenching layers, which are typically positioned between the light-emitting layer and one of the contact layers. A charge transport layer may be a hole transport layer or an electron transport layer or both. A hole transport layer may be positioned between the light-emitting layer and the anode contact layer which provides holes into the light-emitting layer. An electron transport layer may be positioned between the light-emitting layer and the cathode contact layer, which injects electrons into the light-emitting layer.

Charge transport materials are also useful in transport layers acting as photoconductors used in imaging products such as xerography and laser printers. (R. B. Seymour, ed., "Conductive Polymers", Plenum Press, New York, 1981); as molecular transistors (C. R. Kagan, and P. Andry, "Thin Film Transistors, Marcel Dekker, New York, 2003) and as elements in organic photovoltaics (P. Peumans, A. Yakimov, and S. R. Forrest, J. Apply. Phys., 93, 3693 (2003)).

There remains a need for new charge transport materials.

SUMMARY OF THE INVENTION

There is provided a new compound $(Rc-X-)_n Rd$ wherein:
Rc is the same or different at each occurrence and comprises a dibenzo[O,S]furpyran substructure;
X is the same or different at each occurrence and is independently selected from a single bond, an alkylene group, an arylene group, a arylenealkylene group, a heteroalkylene group, a heteroarylene group, a heteroarylenealkylene group, —C(=O)O—, —OC(=O)—, —S—, and an ether group;
Rd is selected from the group consisting of a multivalent alkyl group, a multivalent aryl group, a multivalent heteroalkyl group, a multivalent heteroaryl group, and a multivalent heteroarylalkyl group and
n is an integer from 2 to 6.

In another embodiment, there is provided a new compound CM-1

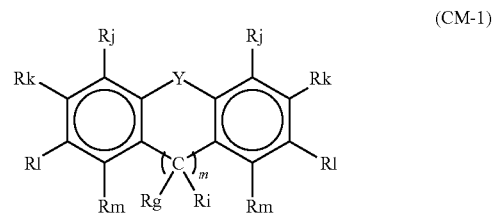

(CM-1)

wherein:
Y is one of S and O;
m is one of 0 and 1; and
at least one of Rg, Ri, Rj, Rk, Rl, and Rm is selected from an alkyl group, aryl group, aralkyl group, heteroalkyl group, and a heteroarylene group.

In another embodiment, there is provided a new charge transport layer comprising one of the above chalcogen compounds.

In another embodiment, there is provided a new electronic device comprising an anode, a cathode, and an active layer interposed between the anode and cathode, and further comprising one of the above chalcogen compounds in a layer selected from the active layer, a charge transport layer interposed between the active layer and the cathode, and combinations thereof.

DETAILED DESCRIPTION

Figure 1:
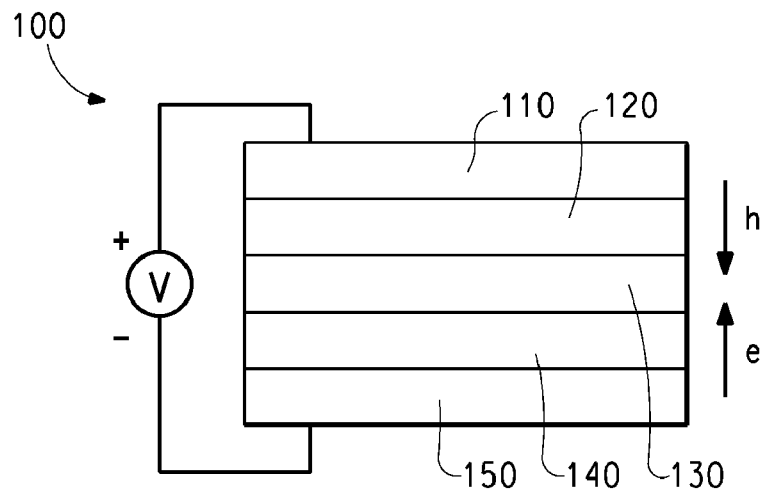
FIG. 1 is a schematic diagram of an electroluminescent device, for example as in a Light-Emitting Diode (LED).

There is provided a new compound $(Rc-X-)_n Rd$ wherein:
Rc is the same or different at each occurrence and comprises a dibenzo[O,S]furpyran substructure;
X is the same or different at each occurrence and is independently selected from a single bond, an alkylene group, an arylene group, a arylenealkylene group, a heteroalkylene group, a heteroarylene group, a heteroarylenealkylene group, —C(=O)O—, —OC(=O)—, —S—, and an ether group;
Rd is selected from the group consisting of a multivalent alkyl group, a multivalent aryl group, a multivalent heteroalkyl group, a multivalent heteroaryl group, and a multivalent heteroarylalkyl group and
n is an integer from 2 to 6.

As used herein, the term "dibenzo[O,S]furpyran substructure" indicates a substructure selected from the group consisting of the dibenzofuran substructure (SS-2), the dibenzothiophene substructure (SS-3), the dibenzopyran substructure (SS-4), and the dibenzothiapyran substructure (SS-5).

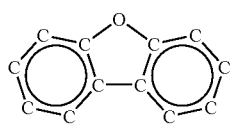
(SS-2)

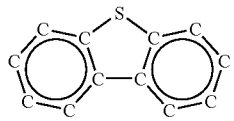
(SS-3)

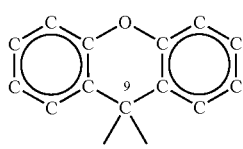
(SS-4)

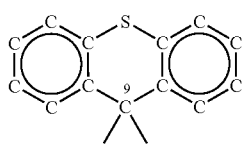
(SS-5)

Note that in both the two pyran substructures, the single non-aromatic carbon designated as C-nine is required to have four separate atoms bonded to it, as denoted by four single bonds. A compound including at least one of the dibenzofuran substructure, the dibenzothiophene substructure, the dibenzopyran and the dibenzothiapyran substructure can be designated as a dibenzo[O,S]furpyran compound, regardless of how many times in the compound any particular dibenzo[O,S]furpyran substructure occurs, and regardless of how many other atoms such as hydrogen occur. The number of hydrogens attached to these four substructures is unspecified.

As used herein, the term "multivalent" is intended to mean having more than one point of attachment.

Dibenzo[O,S]furpyran substructures can be substituted at any position by other groups including but not limited at least one instance of a group chosen from the group consisting of an acetal, ketal, carboxylic acid, carboxylate salt, carboxylate ester, alcohol, aldehyde, chloro, fluoro, bromo, iodo, amide, ketone, amine, silyl, carbamate, nitro, epoxide, ether, thioether, sulfonamide, sulfone, sulfonic acid, sulfonate salt, sulfonic ester, sulfone, sulfonamide, sulfoxide, thioamide, triazine, nitrile, and other conventional groups.

Examples of compounds having the formula (Rc-X-)$_n$Rd include but are not limited to CM-6, CM-7, CM-8, CM-9, CM-10, CM-11, CM-12, CM-13, and CM-14.

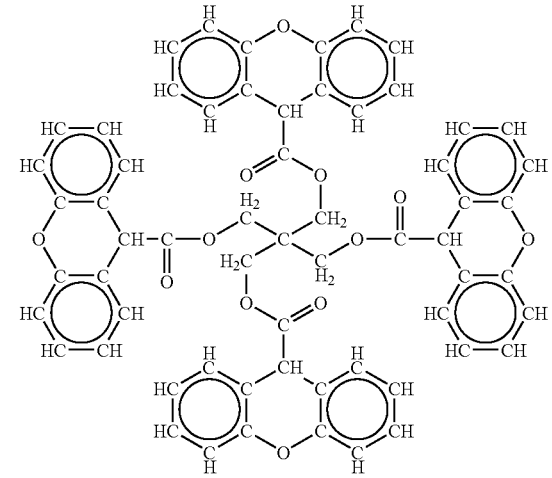
(CM-6)

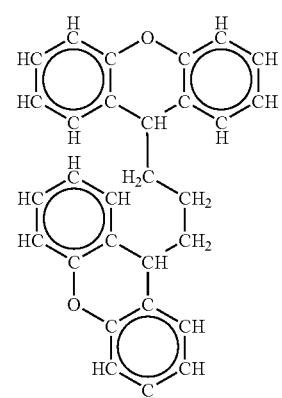
(CM-7)

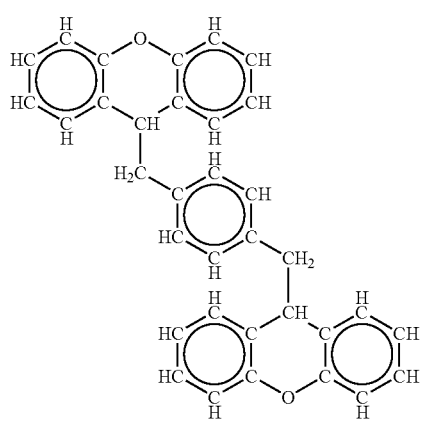
(CM-8)

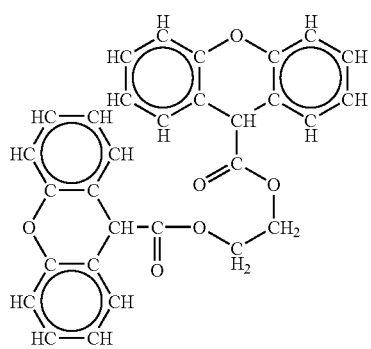
(CM-9)

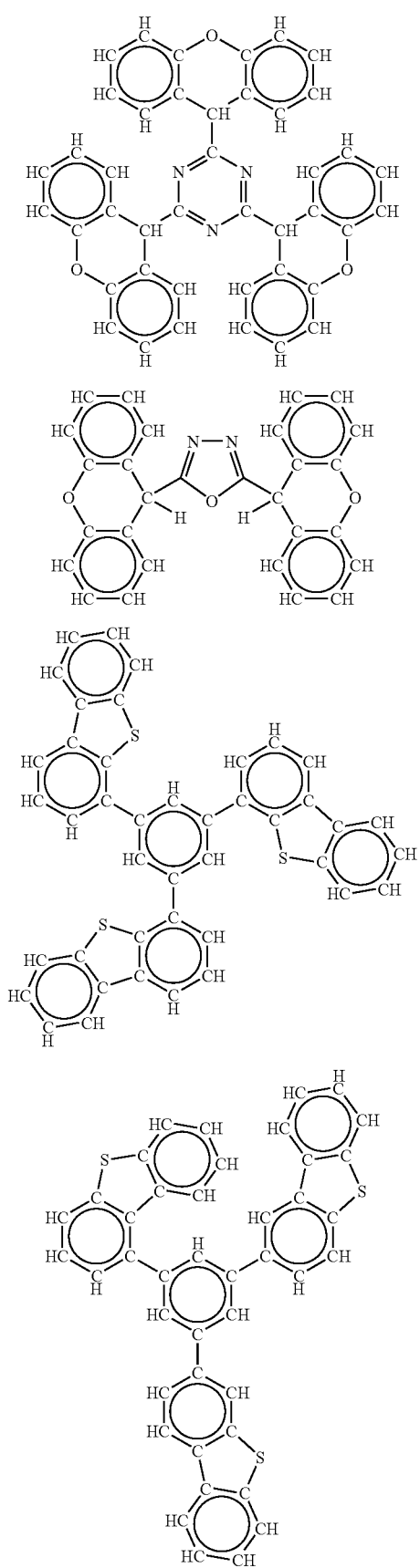

(CM-10)
(CM-11)
(CM-12)
(CM-13)

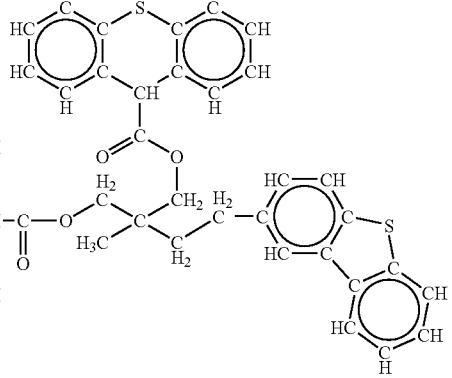

(CM-14)

A tetraester made by conventional esterification, CM-6 includes four instances of the dibenzopyran substructure. CM-13 includes three instances of the dibenzothiafuran substructure, each instance being a different positional substitution. In CM-6, $M_r$~968, the relative mass percent of dibenzopyran substructure ($M_r$~172) is ~71%. In CM-14, $M_r$~732, the relative mass percent of dibenzopyran substructure ($M_r$~172) is ~24%, the relative mass percent of dibenzothiapyran substructure ($M_r$~188) is ~26%, the relative mass percent of dibenzothiofuran substructure ($M_r$~160) is ~22%, and the relative mass percent of all dibenzo[O,S]furpyran groups is ~71%.

In one embodiment, there is provided a new compound CM-1

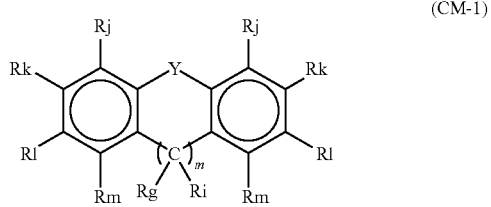

(CM-1)

wherein:

Y is one of S and O;

m is one of 0 and 1; and at least one of Rg, Ri, Rj, Rk, Rl, and Rm is selected from an alkyl group, aryl group, aralkyl group, heteroalkyl group, and a heteroarylene group.

In one embodiment, at least one of Rg, Ri, Rj, Rk, Rl, and Rm is selected from the group consisting of a fluorine atom, chlorine atom bromine atom, methyl group, ethyl group, n-propyl group, iso-propyl group, n-butyl group, iso-butyl group, sec-butyl group, tert-butyl group, phenyl group, nitrile group, nitro group, hydroxyl group, methyl ether group, ethyl ether group, carboxylic acid group and carboxylic ester group consisting of one of methyl, ethyl, n-propyl, iso-propyl, n-butyl, iso-butyl, sec-butyl, tert-butyl, and phenyl esters. In one embodiment, none of Rg, Ri, Rj, Rk, Rl, and Rm comprises a dibenzo[O,S]furpyran substructure.

Examples of CM-1 compounds include, but are not limited to, CM-15, CM-16, and CM-17 below.

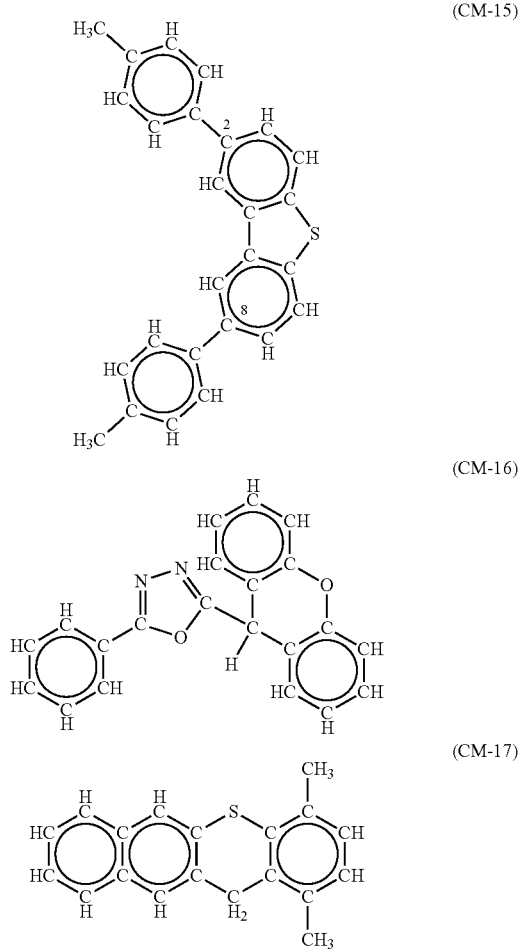

(CM-15)

(CM-16)

(CM-17)

In one embodiment, the chalcogen compound has at least two asymmetric carbon atoms in its structure. In one embodiment, the chalcogen compound has exactly one asymmetric carbon atom in its structure. In one embodiment, the chalcogen compound has no asymmetric carbon atom in its structure.

In one embodiment, the chalcogen compound is a charge transport material. In one embodiment, the chalcogen compound is an electron transport material. Certain substructures or atoms are known on occasion to confer on a compound a utility to transport holes or to electroluminesce. Examples include the carbazole substructure; the triarylamine substructure; the biphenyl-bistriazene substructure; atoms including iridium, platinum, palladium, and rhodium; and extended conjugated substructures with vinylene linkages. Such substructures can, but do not always, interfere with some preferred function that an electron transport compound would have in the absence of the substructures, such as minimizing hole-electron recombination or minimizing electroluminesence that can interfere with electroluminesence by the active compound. For this reason, in one embodiment the chalcogen compound is free of any such substructure (in combination, or singly) and their positional isomers.

In one embodiment, there is provided a new charge transport layer comprising a compound selected from (Rc-X-)$_n$Rd and CM-1, as defined above. As used herein, the term "charge transport" is intended to refer to material or a layer containing material that can receive a charge from an electrode and facilitate its movement through the thickness of the material with relatively high efficiency and small loss of charge. Hole transport compositions are capable of receiving a positive charge from an anode and transporting it. Electron transport compositions are capable of receiving a negative charge from a cathode and transporting it.

In one embodiment, the chalcogen compound includes at least one additional substructure chosen from the group consisting of
an alkyl substructure having 1 to 20 carbons,
a heteroalkyl substructure having 1 to 20 carbons and 1 to 5 heteroatoms,
an alkenyl substructure having 1 to 20 carbons,
a heteroalkenyl substructure having 1 to 20 carbons and 1 to 5 heteroatoms,
an alkynyl substructure having 1 to 20 carbons,
a heteroalkynyl substructure having 1 to 20 carbons and 1 to 5 heteroatoms,
an aryl substructure having 6 to 30 carbons,
a heteroaryl substructure having 6 to 30 carbons and 1 to 5 heteroatoms,
each substructure having from one to six substituents that are not hydrogen, with all remaining substituents being hydrogen, and the heteroatoms being the same or different, and chosen from the heteroatom group of boron, nitrogen, oxygen, silicon, phosphorous, and sulfur,
and combinations built up from these substructures.

In one embodiment, the chalcogen compound includes at least one additional substituent chosen from the group consisting of an acetal, ketal, carboxylic acid, carboxylate salt, carboxylate ester, alcohol, aldehyde, chloro, fluoro, bromo, iodo, amide, ketone, amine, silyl, carbamate, nitro, epoxide, ether, thioether, sulfonamide, sulfone, sulfonic acid, sulfonate salt, sulfonic ester, sulfone, sulfonamide, sulfoxide, thioamide, triazine, nitrile, and other conventional groups.

In one embodiment, the chalcogen compound includes between 1 and 10 (inclusive) instances of at least one dibenzo[O,S]furpyran substructure. In one embodiment, the chalcogen compound includes between 1 and 10 (inclusive) instances of exactly one dibenzo[O,S]furpyran substructure. In one embodiment, the chalcogen compound includes between 1 and 10 (inclusive) instances of exactly two dibenzo[O,S]furpyran substructures. In one embodiment, the relative mass percent of any present dibenzo[O,S]furpyran substructure in the chalcogen compound is greater than one of 0.1%. In one embodiment, it is greater than 10%. In one embodiment it is greater 30%. In one embodiment it is greater than 50%. In one embodiment it is greater than 70%. In one embodiment, the relative mass percent of a single chalcogen compound in a layer is greater than 10%. In one embodiment, it is greater than 10%. In one embodiment it is greater 30%. In one embodiment it is greater than 50%. In one embodiment it is greater than 70%.

In some instances, a low relative molecular mass of the chalcogen compound is advantageous, for example for vapor deposition and dissolution for solution application. In one embodiment, the relative molecular mass of the chalcogen compound is less than 100,000. In one embodiment, the mass is less than 30,000. In one embodiment, the relative molecular mass is less than 1000. In some instances, a high relative molecular mass chalcogen compound is advantageous, for example to minimize interlayer migration and to provide a plastic rather than a crystalline layer.

In another embodiment, there is provided a new electronic device comprising an anode, a cathode, and an active layer interposed between the anode and cathode, and further comprising one of the above compounds in a layer selected from the active layer, a charge transport layer interposed between the active layer and the cathode, and combinations thereof.

The term "electronic device" is intended to mean a collection of circuits, electronic components, or combinations thereof that collectively, when properly connected and supplied with the appropriate potential(s), performs a function. An electronic device may include or be part of a system. An example of an electronic device includes a display, a sensor array, a computer system, avionics, an automobile, a cellular phone, another consumer or industrial electronic product, or the like.

Electronic devices that may benefit from having one or more layers comprising the chalcogen compounds discussed above include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode), or any combination of devices in items (1) through (4).

One illustration of an electronic device structure is shown in FIG. 1. The device 100 has an anode layer 110 and a cathode layer 160, and a photoactive layer 130 between them. Adjacent to the anode is a layer 120 comprising hole transport material. Adjacent to the cathode is a layer 140 comprising an electron transport material. As an option, devices frequently use another electron transport layer or electron injection layer 150, next to the cathode.

Compounds disclosed herein can be utilized in one or more of an active layer 130 and an electron transport layer 140. While not wishing to be bound by any particular theory, it is believed that these compounds are good electron transporters and have a high triplet energy which does not promote quenching of activated active compounds.

In one embodiment, the above-described chalcogen compounds can function as a host for the photoactive material in layer 130. When present as a host, the chalcogen compound should be physically compatible with the photoactive material, so that the materials do not separate into separate phases. The host is generally present in an amount greater than 50% by weight, based on the total weight of the photoactive layer. In one embodiment, the host is present in an amount greater than 60% by weight. In one embodiment, the host is present in an amount greater than 75% by weight. The chalcogen compound and photoactive material can be applied by a vapor co-deposition process, when applicable, by a solution deposition process from a common solution, or by a thermal transfer process.

In one embodiment, the above-described chalcogen compounds can function as an electron transport material, hole blocking material, anti-quenching material, or combinations thereof, in layer 140. As used herein, the term "electron transport" means when referring to a layer, material, member or structure, such a layer, material, member or structure that promotes or facilitates migration of negative charges through such a layer, material, member or structure into another layer, material, member or structure. The term "hole blocking" is intended to mean a material, layer, member or structure which prevents, retards, or diminishes the migration of negative charges through such a layer, material, member or structure into another layer, material, member or structure. The term "anti-quenching material" is intended to mean a material which prevents, retards, or diminishes both the transfer of energy and the transfer of an electron to or from the excited state of the photoactive layer to an adjacent layer. The chalcogen compound can be applied by a vapor deposition process, when applicable, by a solution deposition process, or by a thermal transfer process.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature vol.* 357, pp 477-479 (11 Jun. 1992). At least one of the anode and cathode should be at least partially transparent to allow the generated light to be observed.

Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules include, but are not limited to: N,N'-diphenyl-N, N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-Bis(naphthalen-1-yl)-N,N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, poly(dioxythiophenes), and polyaniline. It is also possible to obtain hole transporting polymers by doping hole transporting molecules such as those mentioned above into polymers such as polystyrene and polycarbonate.

Any organic electroluminescent ("EL") material can be used as the photoactive material in layer 130, including, but not limited to, small molecule organic fluorescent compounds, fluorescent and phosphorescent metal complexes, conjugated polymers, and mixtures thereof. Examples of fluorescent compounds include, but are not limited to, pyrene, perylene, rubrene, coumarin, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly (phenylenevinylenes), polyfluorenes, poly(spirobifluorenes), polythiophenes, poly(p-phenylenes), copolymers thereof, and mixtures thereof.

Examples of electron transport materials which can be used in optional layer 150 include, but are not limited to, metal chelated oxinoid compounds, such as bis(2-methyl-8-quinolinolato)(para-phenyl-phenolato)aluminum(III) (BAlQ) and tris(8-hydroxyquinolato)aluminum (Alq$_3$); azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and Li2O can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency with device operational lifetime.

It is understood that each functional layer may be made up of more than one layer.

The device can be prepared by a variety of techniques, including sequentially depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing. any conventional coating or printing technique, including but not limited to spin-coating, dip-coating, roll-to-roll techniques, ink-jet printing, screen-printing, gravure printing and the like.

In one embodiment, the different layers have the following range of thicknesses: anode 110, 50-500 nm, in one embodiment 100-200 nm; hole transport layer 120, 5-200 nm, in one embodiment 20-100 nm; photoactive layer 130, 1-200 nm, in one embodiment 10-100 nm; layers 140 and 150, each 5-200 nm, in one embodiment 10-100 nm; cathode 160, 20-1000 nm, in one embodiment 30-500 nm. The location of the electron-hole recombination zone in the device, and thus the emission spectrum of the device, can be affected by the relative thickness of each layer. Thus the thickness of the electron transport layer should be chosen so that the electron-hole recombination zone is in the light-emitting layer. The desired ratio of layer thicknesses will depend on the exact nature of the materials used.

Figure 2:
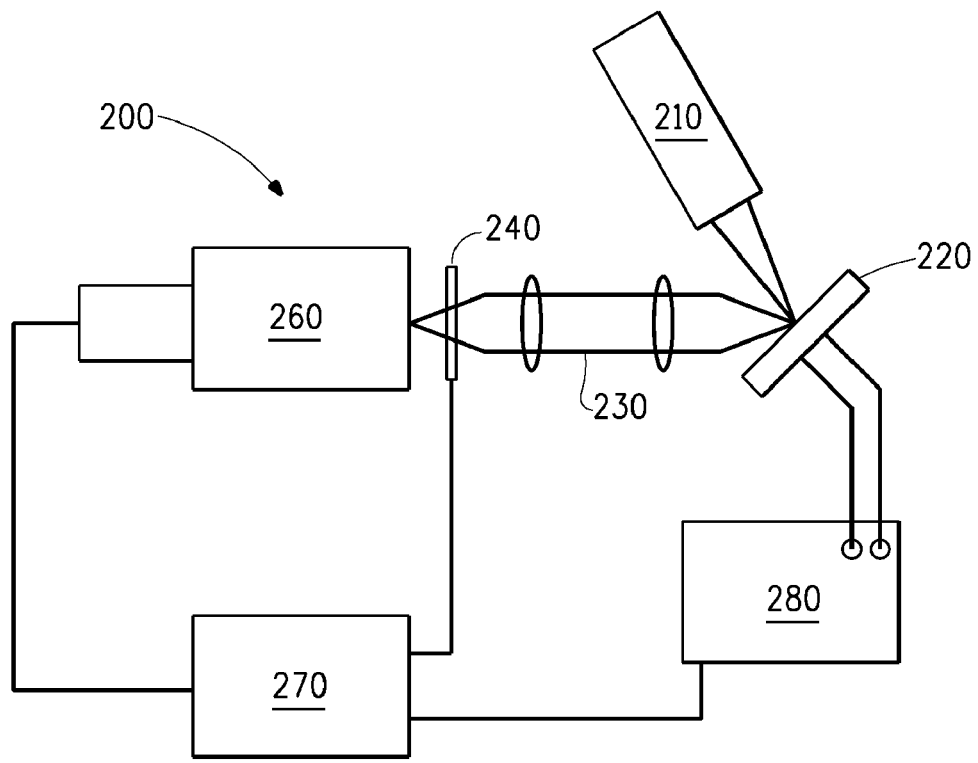
FIG. 2 is a schematic diagram of an LED testing apparatus.

A device may be characterized by measuring (1) current-voltage (I-V) curves, (2) electroluminescence radiance versus voltage, and (3) electroluminescence spectra versus voltage. FIG. 2 shows a suitable apparatus 200. The I-V curves of a device, 220, were measured with an instrument 280 which measures current while sourcing voltage, or measures voltage while sourcing current, such as Keithley Source-Measurement Unit Model 237 (Keithley Instrument, Inc., Cleveland, Ohio). The electroluminescence radiance (in the unit of cd/m2) versus voltage was measured while the voltage was scanned using the instrument 280.

Electroluminescence radiance can be measured with a luminance meter 210, such as the Minolta LS-110 luminescence meter (Konica Minolta Holdings, Tokyo, Japan) having a single lens reflex optical system for precise aiming, capable of an acceptance angle of 0.333° and measurement of 0.01 to about 1 million cd/m2. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the device by the current density needed to run the device. The unit of efficiency is the cd/A.

Other uses for the new chalcogen compounds include coating materials for memory storage devices, antistatic films, biosensors, electrochromic devices, solid electrolyte capacitors, energy storage devices such as a rechargeable battery, and electromagnetic shielding applications.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

The phrase "X is selected from A, B, and C" is equivalent to the phrase "X is selected from the group consisting of A, B, and C", and is intended to mean that X is A, or X is B, X is C, X is A+B, X is B+C, X is A+C, or X is A+B+C. The phrase "X is selected from 1 through n" is intended to mean that X is 1, or X is 2, ... or X is n.

Unless otherwise defined, all technical and scientific terms used herein have the same meaning as commonly understood by one of ordinary skill in the art to which this invention belongs. Although suitable methods and materials are described herein for embodiments of the invention, or methods for making or using the same, other methods and materials similar or equivalent to those described can be used without departing from the scope of the invention. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "group" is intended to mean a part of a compound, such as a substituent in an organic compound. The prefix "hetero" indicates that one or more carbon atoms has been replaced with a different atom.

The term "alkyl" is intended to mean a group derived from an aliphatic hydrocarbon having one point of attachment.

The term "alkylene" is intended to mean a group derived from an aliphatic hydrocarbon and having two or more points of attachment.

The term "alkenyl" is intended to mean a group derived from a hydrocarbon having one or more carbon-carbon double bonds and having one point of attachment. The term "alkynyl" is intended to mean a group derived from a hydrocarbon having one or more carbon-carbon triple bonds and having one point of attachment. The term "alkenylene" is intended to mean a group derived from a hydrocarbon having one or more carbon-carbon double bonds and having two or more points of attachment. The term "alkynylene" is intended to mean a group derived from a hydrocarbon having one or more carbon-carbon triple bonds and having two or more points of attachment.

The term "aryl" is intended to mean a group derived from an aromatic hydrocarbon having one point of attachment.

The term "arylalkylene" is intended to mean a group derived from an alkyl group having an aryl substituent.

The term "arylene" is intended to mean a group derived from an aromatic hydrocarbon having two points of attachment.

The term "arylenealkylene" is intended to mean a group having both aryl and alkyl groups and having at least one point of attachment on an aryl group and at least one point of attachment on an alkyl group. Unless otherwise indicated, all groups can be unsubstituted or substituted. Unless otherwise indicated, all groups can be linear, branched or cyclic, where possible. The phrase "adjacent to," when used to refer to layers in a device, does not necessarily mean that one layer is immediately next to another layer. On the other hand, the phrase "adjacent R groups," is used to refer to R groups that are next to each other in a chemical formula (I.e., R groups that are on atoms joined by a bond). Group numbers corresponding to columns within the periodic table of the elements use the "New Notation" convention as seen in the CRC Handbook of Chemistry and Physics, 81st Edition (2000), where the groups are numbered from left to right as 1-18.

The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic atom or ion. The term "complex", when used as a noun, is intended to mean a compound having at least one metallic atom or ion and at least one ligand.

The term "polymer" is intended to mean a material having at least one repeating monomeric unit. The term includes homopolymers having only one kind of monomeric unit, and copolymers having two or more different monomeric units. Copolymers are a subset of polymers. In one embodiment, a polymer has at least 5 repeating units. The term "polymeric" is intended to encompass any combination of linear, cyclic, branched, hyperbranched, oligomeric and similar species, and include species derived by one or more of condensation, ring-opening, addition and similar polymerization methods of at least one monomer (thereby also encompassing copolymeric species).

A polymer composition is typically is a collection of species of different relative molecular mass, the specific mass of each species depending on the number and identity of the monomers, initiating fragment, and termination mechanism. A polymer is therefore typically a collection of compounds of closely related structure, differing in relative molecular mass in a predictable fashion.

A "substructure" is intended to encompass a chemical structure with at least one atom unspecified. Bond hybridization can be specified or unspecified. One way in that a substructure can be converted to a fully drawn chemical structure is by specifying one or more atoms. In a multivalent substructure, two or more atoms are missing from a corresponding fully drawn chemical structure—in other words, multiple valences are unsatisfied.

The foregoing general description and the following detailed description are exemplary and explanatory only and are not restrictive of the invention, as defined in the appended claims.

EXAMPLES

The following examples illustrate certain features and advantages of the present invention. They are intended to be illustrative of the invention, but not limiting. Unless otherwise specified, all percentages, amounts and parts are by mass.

Example 1

This example illustrates the preparation of Chalcogen compound CM-6.

Pentaerythritol (272 parts) was reacted with 9H-xanthene-9-carboxylic acid (2260 parts) and a small catalytic amount of p-toluene sulfonic acid in refluxing toluene (26000 parts) at reflux for 18 hours, during which time generated water was removed using a trap under conventional conditions. Cooling to 25° C. produced a precipitate (discarded). Chromatography through silica gel, eluted by dichloromethane-hexane (70-30) gave CM-6 (1620 parts) as confirmed by 1H-NMR and 13C-NMR.

Example 2

This Example illustrates the preparation of Chalcogen compound CM-7.

Using conventional anhydrous techniques in a nitrogen atmosphere, dibenzopyran (1000 parts) in tetrahydrofuran (13350 parts) was deprotonated by the slow addition of 1.00 molar equivalents based on dibenzopyran of 1.6 M n-butyllithium in hexane at −78° C. followed by a 5 minute hold. While maintaining the reaction temperature at −78° C., 550 parts 1,3-dibromopropane was added. Thereafter the mixture was allowed to warm to 25° C. The tetrahydrofuran was removed at reduced pressure. The resulting residue was partitioned between water and dichloromethane. The dichloromethane layer was washed successively with aqueous 5% sodium bicarbonate and saturated aqueous sodium chloride brine and then dried over anhydrous magnesium sulfate and concentrated using vacuum to give a second residue. The second residue, a white solid, was purified chromatographically using silica gel eluted with 4% ethyl acetate in hexanes to give the 441 parts CM-7 having the appropriate 1H-NMR and 13C-NMR.

Example 3

This Example illustrates the preparation of Chalcogen compound CM-8.

Using conventional anhydrous techniques in a nitrogen atmosphere, dibenzopyran (2000 parts) in tetrahydrofuran (13350 parts) was deprotonated by the slow addition of 0.99 molar equivalents based on dibenzopyran of 1.6 M n-butyllithium in hexane at −78° C. followed by a 5 minute hold. While maintaining the reaction temperature at −78° C., 1159 parts 1,4-bis(bromomethyl)benzene (i.e. p-xylylene dibromide) in 8900 parts tetrahydrofuran was added at a steady rate over 15 minutes. The mixture was maintained at a temperature of −70° C. for 1 hour. Thereafter the mixture was allowed to warm to 25° C. and was maintained at a temperature of 25° C. for 30 minutes. The reaction was quenched by addition of ethyl acetate. The tetrahydrofuran was removed at reduced pressure. The resulting residue was partitioned between water and dichloromethane. The dichloromethane layer was dried over anhydrous sodium sulfate and concentrated using vacuum to give a 1300 parts of second residue. The second residue, a white solid, was purified by recrystallization from dichloromethane/isopropanol to provide 635 parts of white crystalline CM-8 having the appropriate 1H-NMR and 13C-NMR.

Example 4

This Example illustrates the preparation of Chalcogen compound CM-9.

Ethylene glycol (621 parts) was reacted with 9H-xanthene-9-carboxylic acid (6790 parts) and a small catalytic amount of p-toluene sulfonic acid in refluxing toluene (17300 parts) at reflux under conventional conditions until water removal to a trap had ceased. The reaction mixture was partitioned between toluene and aqueous sodium bicarbonate to remove unreacted acid. Concentration of the toluene solution and chromatography of the residue gave CM-9 (4350 parts) as confirmed by 1H-NMR and 13C-NMR.

Example 5

This Example illustrate the preparation of Chalcogen compound CM-10.

Using conventional anhydrous techniques in a nitrogen atmosphere, dibenzopyran (300 parts) in tetrahydrofuran (2670 parts) was deprotonated by the slow addition of 0.97 molar equivalents of 1.6 M n-butyllithium in hexane at −78° C. While maintaining the reaction temperature at −78° C., 92 parts cyanuric chloride was added. Thereafter the mixture was allowed to warm to 25° C., and kept at 25° C. for three hours followed by addition of ethyl acetate and water (5000 parts). Chromatographic purification yielded a red oil having the appropriate analytical characteristics for CM-10.

Example 6

This Example illustrates the preparation of Chalcogen compound CM-11.

Under an atmosphere of nitrogen, a reactor was charged sequentially with 180 parts 9H-xanthene-9-carboxylic acid, 200 parts of 9-dibenzopyrancarboxylic hydrazide and 9870 parts phosphorus (V) trichloride oxide and the resulting mixture was heated to reflux for 67 hours and then cooled to 25° C. and poured into an excess of ice water and neutralized with 4 Normal aqueous NaOH. The resulting gray solid was collected by filtration, washed with water and dried. The clean dry solid was purified by recrystallization to provide 75.2 parts of CM-11 as demonstrated by liquid chromatography-mass spectrometry, 1H-NMR and 13C-NMR.

Example 7

This Example illustrates the preparation of Chalcogen compound CM-15.

Under an atmosphere of nitrogen, a reactor equipped with a condenser was charged with 2,8-dibromodibenzothiophene (1692 parts), p-tolylboronic acid (1489 parts), tetrakis(triphenylphosphine)palladium (583 parts), 1,4-dioxane (25850 parts) and aqueous solution of potassium carbonate (2066 parts in 6000 parts water). The resulting mixture was heated to reflux for eight days. After cooling to 25° C., the reaction mixture was diluted with dichloromethane (266000 parts) and washed with water (3×100000 parts). The organic layer was dried over anhydrous magnesium sulfate and concentrated to dryness. The residue was added to a dichloromethane-methanol mixture to precipitate the product CM-15 (1194 parts) with appropriate analytical characteristics.

Example 8

This Example illustrates the preparation of Chalcogen compound CM-16.

Under an atmosphere of nitrogen, a reactor was charged with 400 parts of 9H-xanthene-9-carboxylic hydrazide and 980 parts of pyridine. The resulting mixture was cooled to 0° C. and 257 parts of benzoylchloride were added slowly. The mixture was allowed to come to 25° C. and was stirred for one hour. The mixture was then heated to 50° C. for 30 minutes. The reaction mixture was cooled to 25° C. and poured over crushed ice resulting in a white solid which was separated, washed with copious amounts of water, and dried to give 670 parts of a white solid. Under an atmosphere of nitrogen, a reactor was charged sequentially with the white solid and 32900 parts phosphorus (V) trichloride oxide and the resulting new mixture was heated to 50° C. for 75 minutes and then cooled to 25° C. The new mixture was poured into an excess of ice water and neutralized with 4 Normal aqueous NaOH. The resulting white precipitate was collected by filtration and washed with water and dried. The clean dry precipitate was purified by chromatography to provide 190 parts of CM-16 as demonstrated by 1H-NMR and 13C-NMR.

Examples 9-12

These Examples illustrate the formation and properties of OLEDs using chalcogen electron transport compounds.
Device Formation Thin film electroluminescent devices including in order an anode, a hole transport layer, an electroluminescent active layer, an electron transport layer, and a cathode were fabricated by the thermal evaporation-deposition technique in an evacuated deposition vacuum chamber. An evaporator with cryopump (Angstrom Engineering, Inc., Cambridge, Ontario, Canada) was used to obtain a suitable vacuum. The base vacuum for all of the thin film deposition was in the range of 0.09 mPa. Five separate reservoirs were available for material to evaporate and deposit at 0.09 mPa without interruption.

Patterned indium tin oxide (ITO) coated glass substrates (Thin Film Devices, Inc, Anaheim, Calif.) were used as the transparent anode. A suitable glass substrate is a display grade alkaline earth boro-aluminosilicate type made by a draw fusion process to achieve a thermal coefficient of expansion of 4.2 E-06/K @ 300 K, a low surface roughness, a thickness of 0.7 mm and thickness variation of less than 0.02 mm, and a waviness of less than 70 nm with a cut-off of 0.8-8 mm (Corning 1737 Display Grade AMLCD Glass, Corning Display Technologies, Corning, N.Y.). The patterned ITO coated glass substrates were composed of Corning 1737 glass coated with 140 nm of ITO coating, with sheet resistance of 30 ohms/square and 80% light transmission, with a pattern allowing multiple devices to be addressed on a single substrate. These patterned ITO coated glass substrates were then cleaned ultrasonically in aqueous detergent solution. The substrates were then rinsed with distilled water, followed by isopropanol, and then degreased in toluene vapor. The cleaned, patterned substrate was then loaded into the vacuum chamber and the chamber was pumped down to 0.09 mPa. The substrate was then further cleaned using an oxygen plasma for about 5-10 minutes. After cleaning, multiple layers of thin films were then deposited sequentially onto the substrate by thermal evaporation. Finally, patterned metal electrodes of aluminum (Al) were deposited through a mask. The thickness of each deposited film was measured during deposition using a thin film deposition controller utilizing an oscillating quartz crystal as the sensor device (Sigma Instruments, Sunil Associates, New Delhi, India). All film thickness reported in the examples are nominal, calculated assuming the density of the material deposited to be one. The completed electroluminescent device was then taken out of the vacuum chamber and characterized immediately without encapsulation. A summary of the device layers and thicknesses is given in the order of deposition. In all examples the anode was ITO as discussed above, and the cathode was Al having a thickness in the range of 70-76 nm. Other materials used include MPMP and emitter E-1 below.

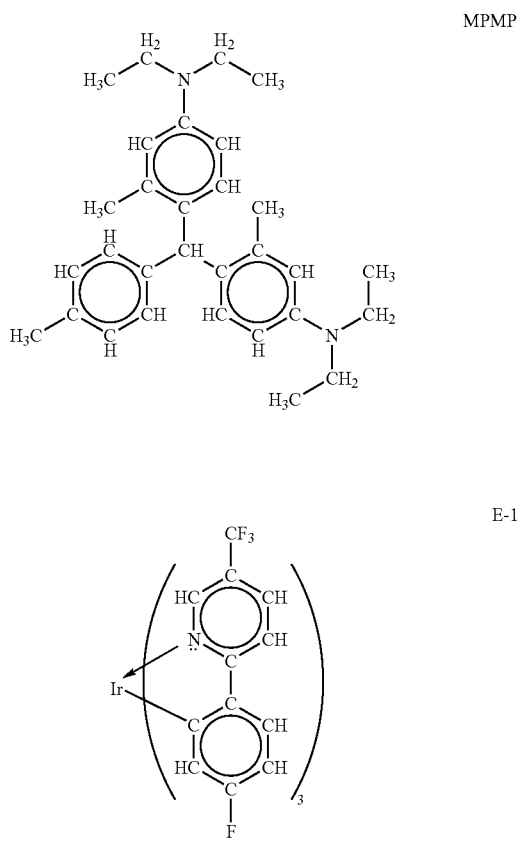

Example 9

The device was made using oxygen plasma cleaned ITO substrate, thereafter depositing a 30.3 nm layer of MPMP, followed by a 40.2 nm layer of electroluminescent compound E-1, followed by a 7.0 nm layer of dibenzothiofuran, followed by a 30.2 nm layer of tris(8-hydroxyquinolato)aluminum (AlQ), followed by 1.0 nm layer of lithium fluoride, followed by 50.5 nm layer of aluminum.

The device had a peak radiance of 6000 cd/m$^2$ at 17 V, and a peak efficiency of 15 cd/A at 15 V.

Example 10

The device was made using oxygen plasma cleaned ITO substrate, thereafter depositing a 30.2 nm layer of MPMP, followed by a 40.3 nm layer of electroluminescent compound E-1, followed by a 10.4 nm layer of CM-15, followed by a 30.4 nm layer of tris(8-hydroxyquinolato)aluminum (AlQ), followed by 1.0 nm layer of lithium fluoride, followed by 50.5 nm layer of aluminum.

The device had a peak radiance of 8000 cd/m$^2$ at 17 V, and a peak efficiency of 18 cd/A at 15 V.

Example 11

The device was made using oxygen plasma cleaned ITO substrate, thereafter depositing a 30.4 nm layer of MPMP, followed by a 40.3 nm layer of electroluminescent compound E-1, followed by a 10.3 nm layer of CM-16, followed by a 30.4 nm layer of tris(8-hydroxyquinolato)aluminum (AlQ), followed by 1.0 nm layer of lithium fluoride, followed by 50.5 nm layer of aluminum.

The device had a peak radiance of 110 cd/m$^2$ at 14 V, and a peak efficiency of 3.5 cd/A at 12 V.

Example 12

The device was made using oxygen plasma cleaned ITO substrate, thereafter depositing a 30.5 nm layer of MPMP, followed by a 40.5 nm layer of electroluminescent compound E-1, followed by a 10.4 nm layer of CM-11, followed by a 30.2 nm layer of tris(8-hydroxyquinolato)aluminum (AlQ), followed by 1.0 nm layer of lithium fluoride, followed by 50.4 nm layer of aluminum.

The device had a peak radiance of 1700 cd/m$^2$ at 17 V, and a peak efficiency of 18 cd/A at 12 V.

What is claimed is:

1. A device comprising an anode, a cathode, and an active layer interposed between the anode and cathode, and further comprising a charge transport compound that comprises at least one dibenzothiapyran group having substructure (SS-5) in a layer selected from the active layer, a charge transport layer interposed between the active layer and the cathode, and combinations thereof:

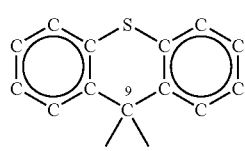
(SS-5)

wherein the single non-aromatic carbon designated as C-nine has four separate atoms bonded to it.

2. A device according to claim 1, wherein the charge transport compound includes 2 to 10 instances of a dibenzothiapyran substructure.

3. A device according to claim 1, wherein charge transport compound comprises (Rc-X-)$_n$Rd wherein:

Rc is the same or different at each occurrence and comprises a dibenzothiapyran having said substructure (SS-5);

X is the same or different at each occurrence and is independently selected from a single bond, an alkylene group, an arylene group, a arylenealkylene group, a heteroalkylene group, a heteroarylene group, a heteroarylenealkylene group, —C(=O)O—, —OC(=O)—, —S—, and an ether group;

Rd is selected from the group consisting of a multivalent alkyl group, a multivalent aryl group, a multivalent heteroalkyl group, a multivalent heteroaryl group, and a multivalent heteroarylalkyl group and n is an integer from 2 to 6.

4. A device according to claim 1, wherein the charge transport compound comprises a compound

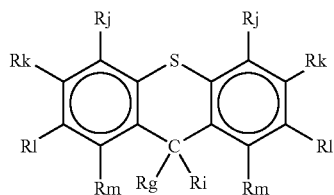

wherein:
at least one of Rg, Ri, Rj, Rk, Rl, and Rm is selected from an alkyl group, aryl group, aralkyl group, heteroalkyl group, and a heteroarylene group.

5. A device according to claim 4, wherein the charge transport compound is free of substructures selected from carbazole substructures, tertiary aromatic amine substructures, triazine substructures, and metal coordination compound substructures.

6. A device according to claim 4, wherein the charge transport compound is selected from CM-14 and CM-17

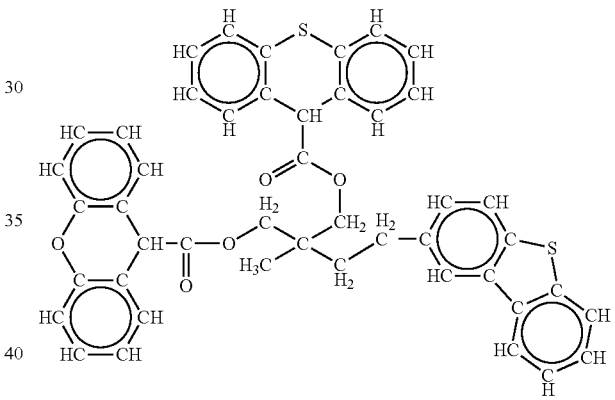
CM-14

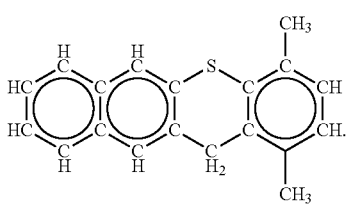
(CM-17)

* * * * *